US008855269B2

(12) United States Patent
Arakita et al.

(10) Patent No.: US 8,855,269 B2
(45) Date of Patent: Oct. 7, 2014

(54) MEDICAL IMAGE DISPLAY APPARATUS AND X-RAY COMPUTED TOMOGRAPHY APPARATUS

(75) Inventors: Kazumasa Arakita, Nasushiobara (JP); Shinsuke Tsukagoshi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 374 days.

(21) Appl. No.: 13/187,832

(22) Filed: Jul. 21, 2011

(65) Prior Publication Data
US 2012/0020452 A1 Jan. 26, 2012

(30) Foreign Application Priority Data

Jul. 22, 2010 (JP) .................................. 2010-165076
Jul. 6, 2011 (JP) .................................. 2011-149759

(51) Int. Cl.
| H05G 1/62 | (2006.01) |
| H05G 1/28 | (2006.01) |
| H05G 1/38 | (2006.01) |
| G01N 23/14 | (2006.01) |
| H04N 5/783 | (2006.01) |
| A61B 6/00 | (2006.01) |
| A61B 6/03 | (2006.01) |
| H04N 9/804 | (2006.01) |
| A61B 8/08 | (2006.01) |
| A61B 5/113 | (2006.01) |

(52) U.S. Cl.
CPC .............. *H04N 5/783* (2013.01); *A61B 8/5284* (2013.01); *A61B 6/5217* (2013.01); *A61B 6/03* (2013.01); *A61B 5/1135* (2013.01); *A61B 6/5288* (2013.01); *A61B 6/486* (2013.01); *H04N 9/804* (2013.01); *A61B 8/5223* (2013.01)
USPC .................................. 378/95; 378/8; 378/165

(58) Field of Classification Search
USPC .............. 378/4–20, 91, 95, 96, 98, 98.8, 162, 378/165, 204, 210, 901
See application file for complete search history.

(56) References Cited

U.S. PATENT DOCUMENTS

| 2003/0035507 A1* | 2/2003 | Hsu et al. .......................... 378/4 |
| 2004/0081269 A1* | 4/2004 | Pan et al. .......................... 378/4 |
| 2008/0107229 A1* | 5/2008 | Thomas et al. .................... 378/4 |

FOREIGN PATENT DOCUMENTS

JP 2010-158275 7/2010

* cited by examiner

*Primary Examiner* — Anastasia Midkiff
(74) *Attorney, Agent, or Firm* — Oblon, Spivak, McClelland, Maier & Neustadt, L.L.P.

(57) ABSTRACT

According to one embodiment, a medical image display apparatus includes an image storage unit configured to store data of a series of medical images constituting a moving image associated with an object, and a reproduction control unit configured to perform read control of the image storage unit to alternately and repeatedly reproduce and display some of the series of medical images corresponding to a partial period in one cycle associated with cyclic motion of the object in a forward direction and a backward direction.

14 Claims, 8 Drawing Sheets

MEDICAL IMAGE DISPLAY APPARATUS AND X-RAY COMPUTED TOMOGRAPHY APPARATUS

CROSS-REFERENCE TO RELATED APPLICATIONS

This application is based upon and claims the benefit of priority from prior Japanese Patent Applications No. 2010-165076, filed Jul. 22, 2010; and No. 2011-149759, filed Jul. 6, 2011, the entire contents of all of which are incorporated herein by reference.

FIELD

Embodiments described herein relate generally to a medical image display apparatus and an X-ray computed tomography apparatus.

BACKGROUND

A method of performing functional analysis by checking tissue dynamics accompanying respiratory motion using a medical image generator such as an X-ray computed tomography apparatus (CT), a magnetic resonance imaging apparatus (MRI), or the like is very effective from the viewpoint of disease diagnosis and early diagnosis. Recently, a technique of repeatedly acquiring volume images covering an entire target tissue and performing multiplanar reconstruction (MPR) or three-dimensional moving image display has been generally used. When observing the lung fields, in particular, it is often a case that a target slice is designated by an MPR image, and its dynamics are observed.

A series of medical images constituting a moving image are chronologically arranged in the order of imaging and repeatedly reproduced. In lung field imaging, it is difficult to perform scanning throughout the entire period of one respiratory cycle because the respiratory cycle is long and there are demands for reduction in radiation exposure. For this reason, scanning is often executed while its period is shorted to a period almost corresponding to a half cycle of respiration. In this case, it is not possible to interpret a tumor or the like throughout the period of one respiratory cycle.

In some cases, a moving image is repeatedly reproduced. In this case, since respiratory phases are distant from each other between the final frame and first frame of the moving image, the visual continuity of the moving image breaks off.

DETAILED DESCRIPTION

In general, according to one embodiment, a medical image display apparatus includes an image storage unit configured to store data of a series of medical images constituting a moving image associated with an object, and a reproduction control unit configured to perform read control of the image storage unit to alternately and repeatedly reproduce and display some of the series of medical images corresponding to a partial period in one cycle associated with cyclic motion of the object in a forward direction and a backward direction.

For example, the above cyclic motion is respiratory motion. A partial period of this respiratory cycle is an inspiratory period or expiratory period. This apparatus acquires a series of images throughout an inspiratory period or expiratory period. The apparatus reproduces the series of acquired images in the forward direction, and then reproduces them in the backward direction. The apparatus repeats this alternate reproduction. This makes it possible to ensure visual continuity. In addition, it is possible to reduce the exposure dose to almost half that when acquiring images throughout the entire period of a respiratory cycle.

A medical image display apparatus according to this embodiment will be described below with reference to the accompanying drawing. Note that the medical image display apparatus is configured to display the moving images generated by an X-ray computed tomography apparatus, a magnetic resonance imaging apparatus (MRI), an ultrasonic diagnostic apparatus, an X-ray diagnostic apparatus, and the like. The medical image display apparatus according to the embodiment is incorporated in such a medical image generator or functions singly. When functioning singly, the medical image display apparatus according to the embodiment is connected to an electrical communication line such as a LAN to receive medical images to be displayed from an in-hospital or out-of-hospital picture archiving and communication system (PACS) via the electrical communication line. Assume that in the following description, the medical image display apparatus is incorporated in an X-ray computed tomography apparatus.

Figure 1:
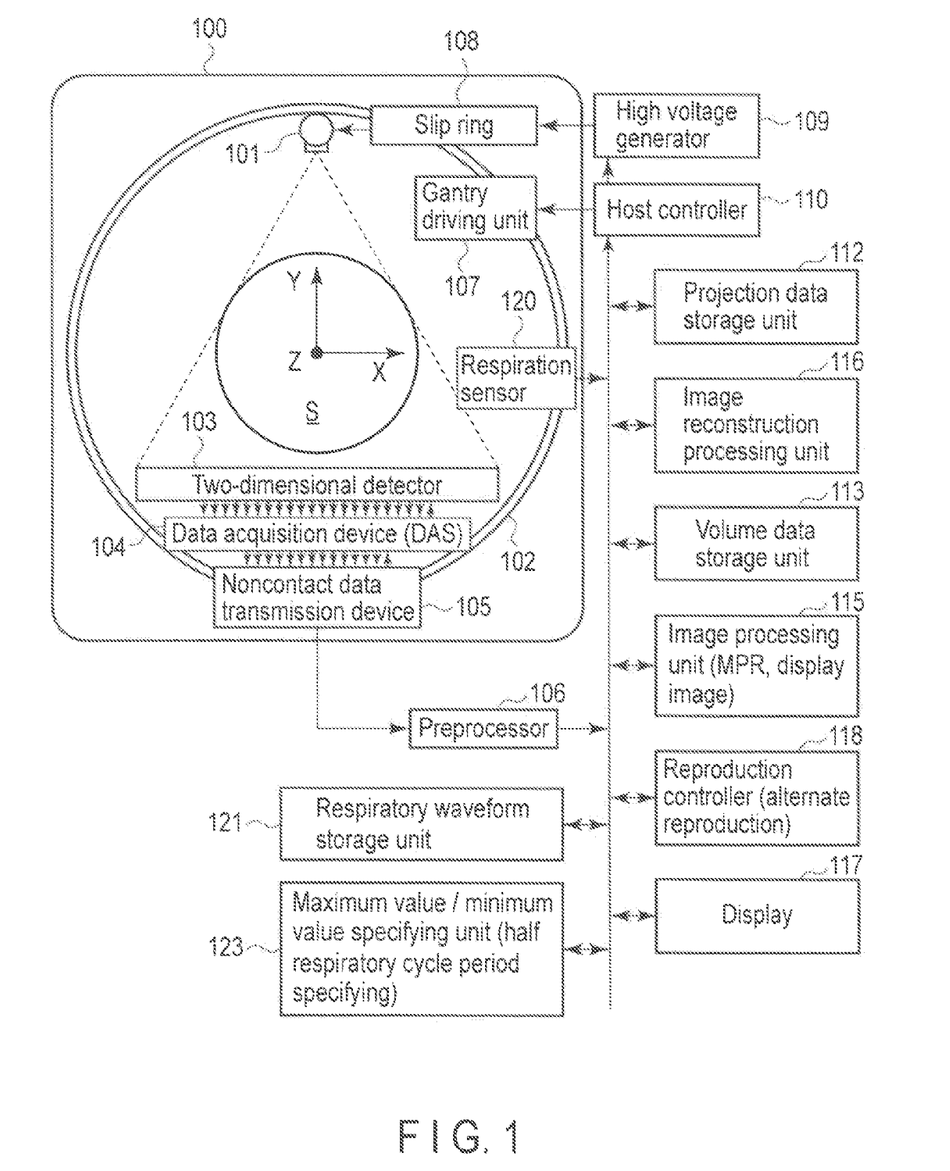
FIG. 1 is a block diagram showing the arrangement of an X-ray computed tomography apparatus including a medical image display apparatus according to an embodiment.

FIG. 1 is a block diagram showing the arrangement of an X-ray computed tomography apparatus including the medical image display apparatus according to this embodiment. A gantry unit 100 includes a rotating frame 102 which is rotatably supported. In the following description, the rotation center axis of the rotating frame 102 is defined as the Z-axis. The gantry unit 100 includes a slip ring 108. A gantry driving unit 107 drives the rotation of the rotating frame 102. A cone beam X-ray tube 101 and a two-dimensional detector 103 are mounted on the rotating frame 102 to face each other through an imaging area S centered on the Z-axis. Although not shown, an object placed on the top of a bed is placed in the imaging area S. The body axis of the object placed on the top almost coincides with the Z-axis. A high voltage generator 109 supplies a tube current to the cone beam X-ray tube 101 and applies a high voltage to it. With this operation, the cone beam X-ray tube 101 generates X-rays in a quadrangular pyramid shape from an X-ray focus F. The two-dimensional detector 103 includes a plurality of X-ray detection element arrays arranged in the shape of an arc centered on the X-ray focus F. The plurality of X-ray detection element arrays are juxtaposed in the Z-axis direction. A data acquisition device 104 generally called a DAS (data acquisition system) is connected to the two-dimensional detector 103.

The cone beam X-ray tube 101 and the two-dimensional detector 103 can acquire projection data in, for example, a wide imaging range including the overall lung fields, by one rotation, while a scan position is fixed. Typically, multislice data or three-dimensional tomographic data can be reconstructed based on the projection data set acquired by one rotation.

For the sake of descriptive convenience, a set of multislice data or three-dimensional tomographic data will be referred to as a "volume data set". In addition, a unit of operation for the acquisition of a projection data set required to reconstruct a volume data set will be referred to as a "volume scan". One volume scan acquires one projection data set. In the following description, assume that one volume data set is reconstructed from one projection data set. Compared with this volume scan, a single scan is defined as a unit of operation for the acquisition of a projection data set required to reconstruct a tomogram associated with a single slice. Although a volume scan will be exemplified here, this embodiment can be applied to a single scan as well as a volume scan. Performing one single scan will acquire one projection data set. The tomographic data set of one slice is reconstructed from one projection data set.

The data acquisition device 104 is provided with, for each channel, an I-V converter for converting the current signal obtained via each channel of the two-dimensional detector 103 into a voltage, an integrator for periodically integrating these voltage signals in synchronism with an X-ray irradiation period, an amplifier for amplifying an output signal from the integrator, and an analog/digital converter for converting an output signal from the amplifier into a digital signal.

A preprocessor 106 is connected to the output of the data acquisition device 104 via a noncontact data transmission device 105 which intermediates optical or magnetic elements. The preprocessor 106 executes preprocessing, for the data detected by the data acquisition device 104, including sensitivity nonuniformity correction processing between channels and the processing of correcting an extreme decrease in signal intensity or signal omission due to an X-ray absorber, mainly a metal portion. A projection data storage unit 112 stores data (projection data) having undergone preprocessing in the preprocessor 106. Attribute information such as a time code corresponding to the data acquisition time, channel number code, view angle code, and the like is associated with the projection data under the control of host controller 110.

An image reconstruction processing unit 116 reconstructs a volume data set based on the projection data set stored in the projection data storage unit 112. A volume data storage unit 113 is provided to store a reconstructed volume data set.

This embodiment executes a so-called 4D dynamic scan under the control of the host controller 110. In a 4D dynamic scan, the apparatus repeats the above volume scan accompanied by continuous rotation of the rotating frame 102. Repeating the volume scan can reconstruct a plurality of volume data sets respectively corresponding to a plurality of imaging times. Typically, the central time of a projection data set used for the reconstruction of a volume data set is specified as an imaging time corresponding to the volume data set. Time codes representing imaging times are respectively associated with a plurality of volume data sets.

Note that the time interval for a plurality of volume data set is the time required for one rotation (scan time), for example, 0.4 sec. It is however possible to extract projection data sets while shifting the rotational angle by 10°, 30°, or the like at a time and generate a plurality of volume data sets, from the projection data sets, with a high time resolution, that is, a time interval shorter than the time required for one rotation, for example, the time required for a 10° rotation or for 30° rotation.

An image processing unit 115 generates the data of a tomogram (MPR image) of an arbitrary slice from a volume data set by so-called MPR processing (multiplanar reconstruction processing) suited to display on an image display unit (display) 117, and also generates the data of a rendering image from a volume data set by so-called rendering processing. In this case, MPR images, rendering images, and other images obtained by conversion to two-dimensional coordinates which are suited to display on the display 117 will be simply referred to as "medical images". The image processing unit 115 uses a plurality of time-series volume data sets obtained by 4D dynamic scanning to generate a series of medical images constituting moving images respectively corresponding to the volume data sets. The volume data storage unit 113 stores the data of the series of medical images generated by the image processing unit 115, together with the volume data sets. The same time codes as those of the volume data sets from which the series of medical images are originated are associated with them, respectively.

A reproduction controller 118 controls reading of medical image data from the volume data storage unit 113 to reproduce and display data in all or part of the period of a series of medical images stored in the volume data storage unit 113 as a moving image. Reproduction/display operation is associated with a cyclic physiological motion of the object. A cyclic physiological motion is typically respiratory motion or heartbeat motion. This embodiment can be applied to both respiratory motion and heartbeat motion. In this case, respiratory motion will be exemplified. For example, a respiration sensor 120 measures the respiratory motion of the object. As is known, respiratory motion is the expansion/contraction of the lung fields accompanying the reciprocal motion of the diaphragm. The abdominal portion reciprocally moves back and forth accompanying the expansion/contraction of the lung fields. The respiration sensor 120 repeatedly measures the distance between the surface of the abdominal portion of the object and an external fixed point (laser irradiation position) by using, for example, a laser distance measurement technique. Temporal changes in this distance represent changes in the respiratory condition (respiratory phase) of the object. The respiration sensor 120 may be the one which has a band-like member wound around the abdominal portion and a pressure sensor mounted between the band-like member and the abdominal portion to allow observation of a respiratory condition from changes in pressure. Alternatively, this sensor may be the one which has a light reflecting member placed on the abdominal portion and captures an image of the member to allow observation of a respiratory condition from the movement of part of the light reflecting member. In addition, the image processing unit 115 may generate a respiratory waveform. For example, temporal changes in the area or volume of a lung field region extracted from an MPR image represent changes in the respiratory condition (respiratory phase) of the object. A respiratory waveform storage unit 121 stores the data of an index such as the above distance, pressure, area, or volume, which represents at least a respiratory condition during the execution of a 4D scan, together with time codes. The time codes associate respiratory index data with medical images.

A maximum value/minimum value specifying unit 123 specifies the maximum and minimum values during the execution of a 4D scan from the stored respiratory index data. For example, the time when the respiratory index exhibits the minimum value represents the expiratory bottom time, whereas the time when the respiratory index exhibits the maximum value represents the inspiratory peak time. The period (inspiratory period) between the expiratory bottom time and the inspiratory peak time represents almost half of a respiratory cycle.

A 4D dynamic scan is executed for a scanning period shorter than the entire period of one respiratory cycle and slightly longer than a half respiratory cycle. A 4D dynamic scanning period is preferably set to half of the entire period of one respiratory cycle. This half period is typically an expiratory period. 4D dynamic scanning is executed only within an inspiratory period by, for example, a respiratory gated technique. No 4D dynamic scanning is executed in an expiratory period. Obviously, it is possible to execute 4D dynamic scanning only within an expiratory period without performing 4D dynamic scanning in an inspiratory period.

This apparatus reconstructs n volume data sets based on the projection data acquired during the execution of this 4D dynamic scan. The apparatus then generates the data of n-frame medical images corresponding to the n volume data. The volume data storage unit 113 stores the data of the n-frame medical images together with the corresponding time codes.

Figure 2:
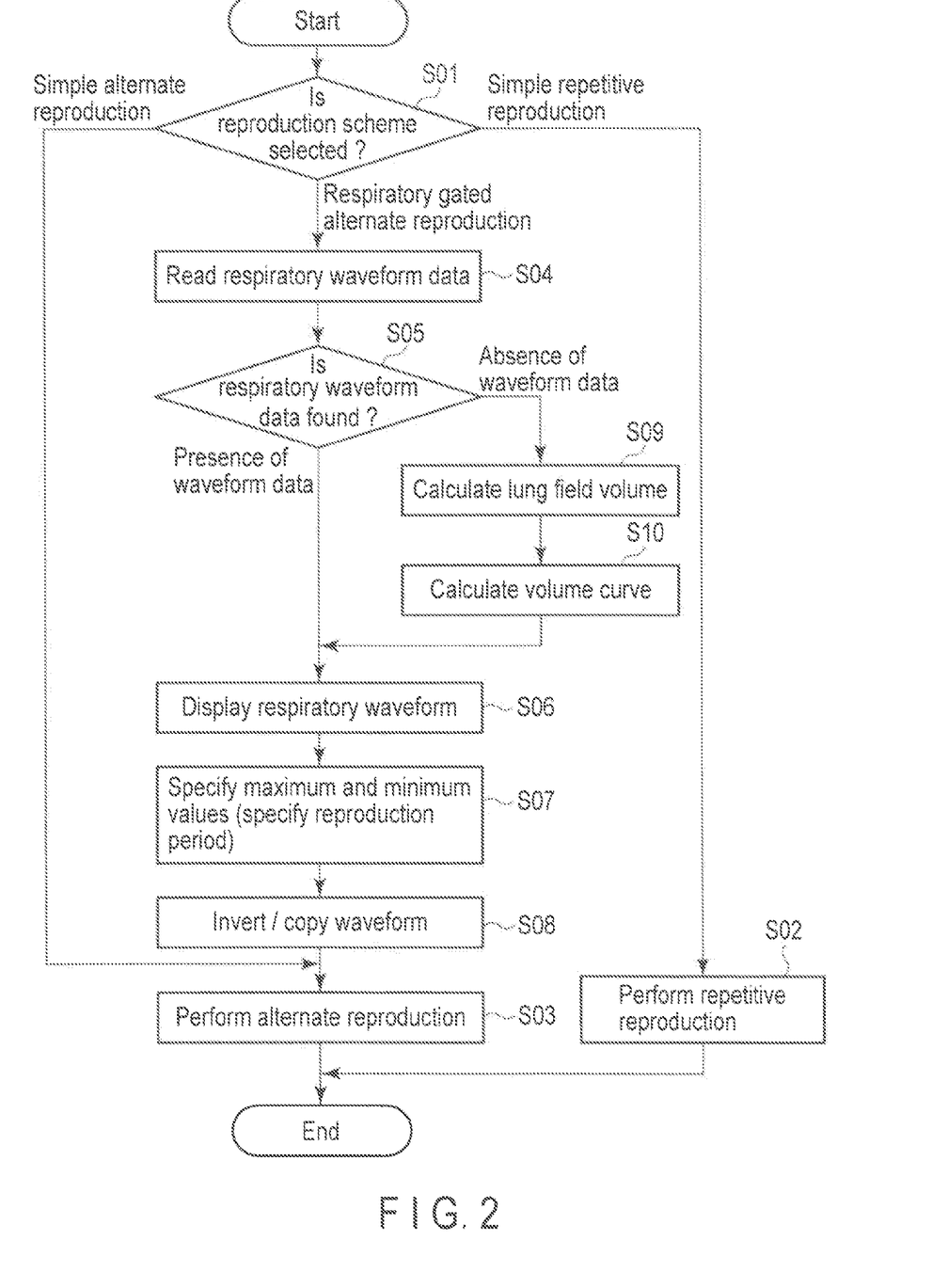
FIG. 2 is a flowchart showing a processing procedure in this embodiment.

The reproduction controller 118 is equipped with three types of reproduction schemes. The three types of reproduction schemes include the simple repetitive reproduction scheme, the simple alternate reproduction scheme, and the respiratory gated alternative reproduction scheme. As shown in FIG. 2, the operator selects one of the three types of reproduction schemes with an input operation device (not shown) (S01).

Figure 3:
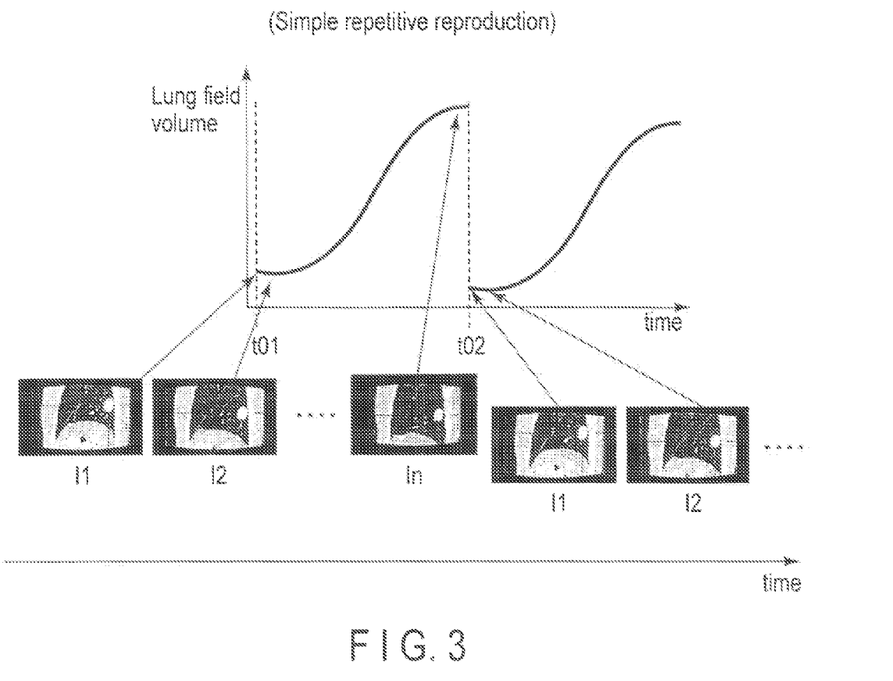
FIG. 3 is a view for explaining simple repetitive reproduction in FIG. 2.

As shown in FIG. 3, in the simple repetitive reproduction scheme, the apparatus repeats the operation of reproducing all the generated n-frame medical images corresponding to the entire period of a 4D dynamic scan, in accordance with the respective time codes, in real time in the forward direction following the same time course as that in the acquisition of image data (S02). The simple repetitive reproduction scheme corresponds to the conventional scheme. The apparatus connects respiratory waveform curves corresponding to the entire period (t01 to t02) of a 4D dynamic scan in accordance with the respiratory waveform data stored in the respiratory waveform storage unit 121, and displays the resultant data on the screen of the display 117, together with a moving image.

Figure 4:
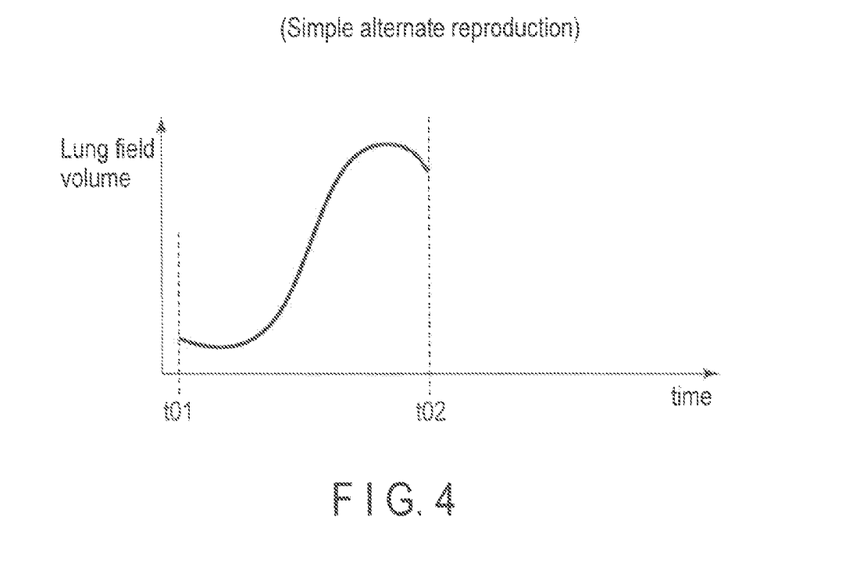
FIG. 4 is a graph showing a scanning period for the explanation of simple alternate reproduction in FIG. 2.
Figure 5:
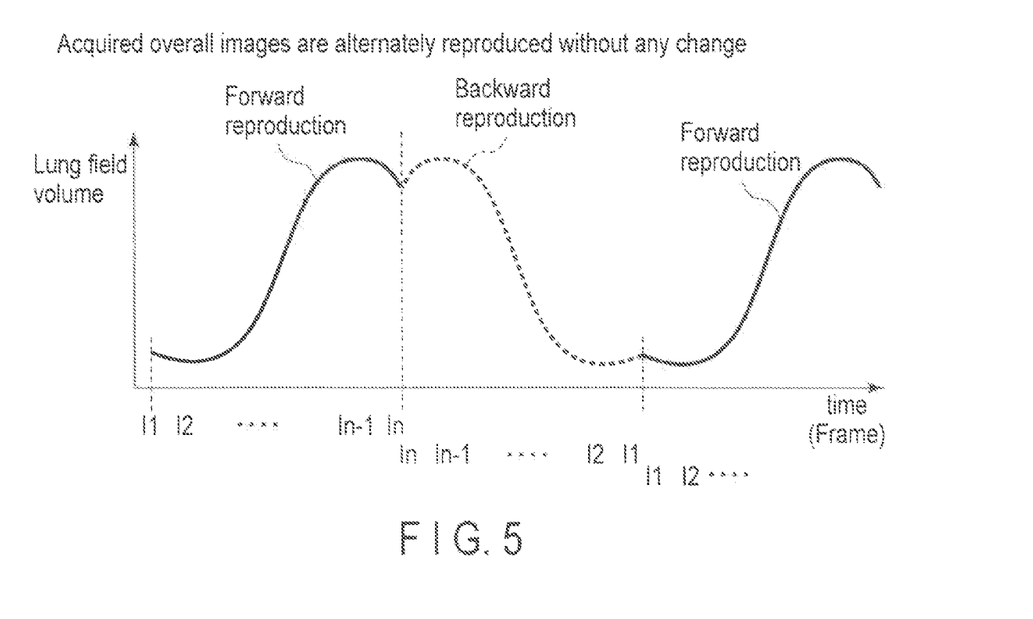
FIG. 5 is a graph for explaining simple alternate reproduction in FIG. 2.

As shown in FIGS. 4 and 5, in the simple alternate reproduction scheme, the apparatus reproduces all the generated n-frame medical images corresponding to the entire period (t01 to t02) of a 4D dynamic scan, in accordance with the respective time codes, in real time in the forward direction following the same time course as that in the acquisition of image data (forward reproduction), and then reproduces the n-frame medical images, in accordance with the time codes, in real time in the backward direction following the time course opposite to that in the acquisition of image data (backward reproduction), thus alternately repeating forward reproduction and backward reproduction in the above manner (S03). The apparatus alternately connects respiratory waveform curves corresponding to the entire period of the 4D dynamic scan stored in the respiratory waveform storage unit 121 in the forward and backward directions, and displays the resultant data on the screen of the display 117, together with a moving image. For example, the respiratory waveform curve generated in the forward direction following the same time course as that in the acquisition of image data is displayed in solid line, whereas the respiratory waveform curve generated in the backward direction following the time course opposite to that in the acquisition of image data is displayed in dotted line.

Figure 6:
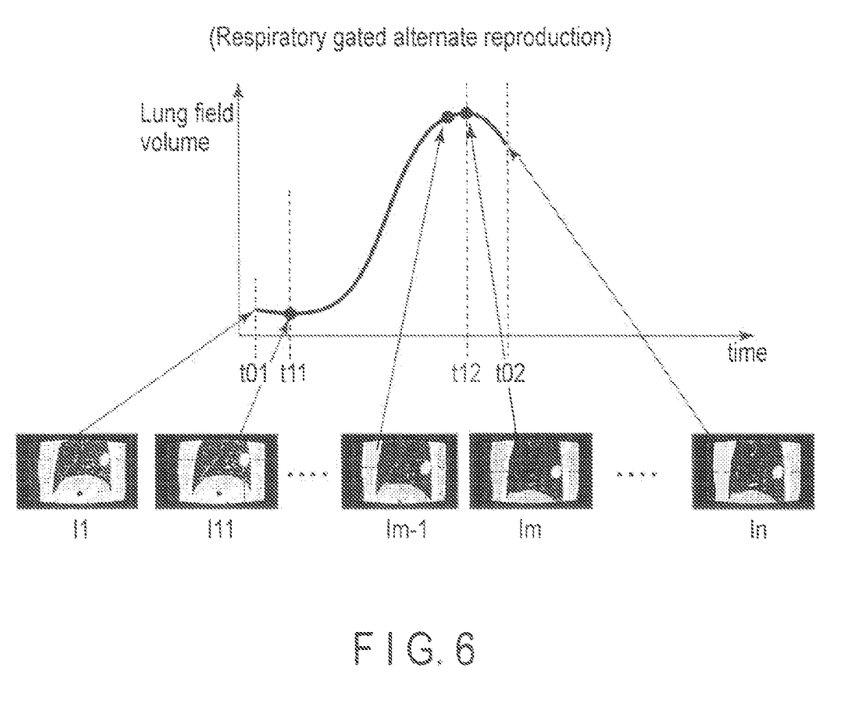
FIG. 6 is a view showing a scanning period for the explanation of respiratory gated alternate reproduction in FIG. 2.
Figure 7:
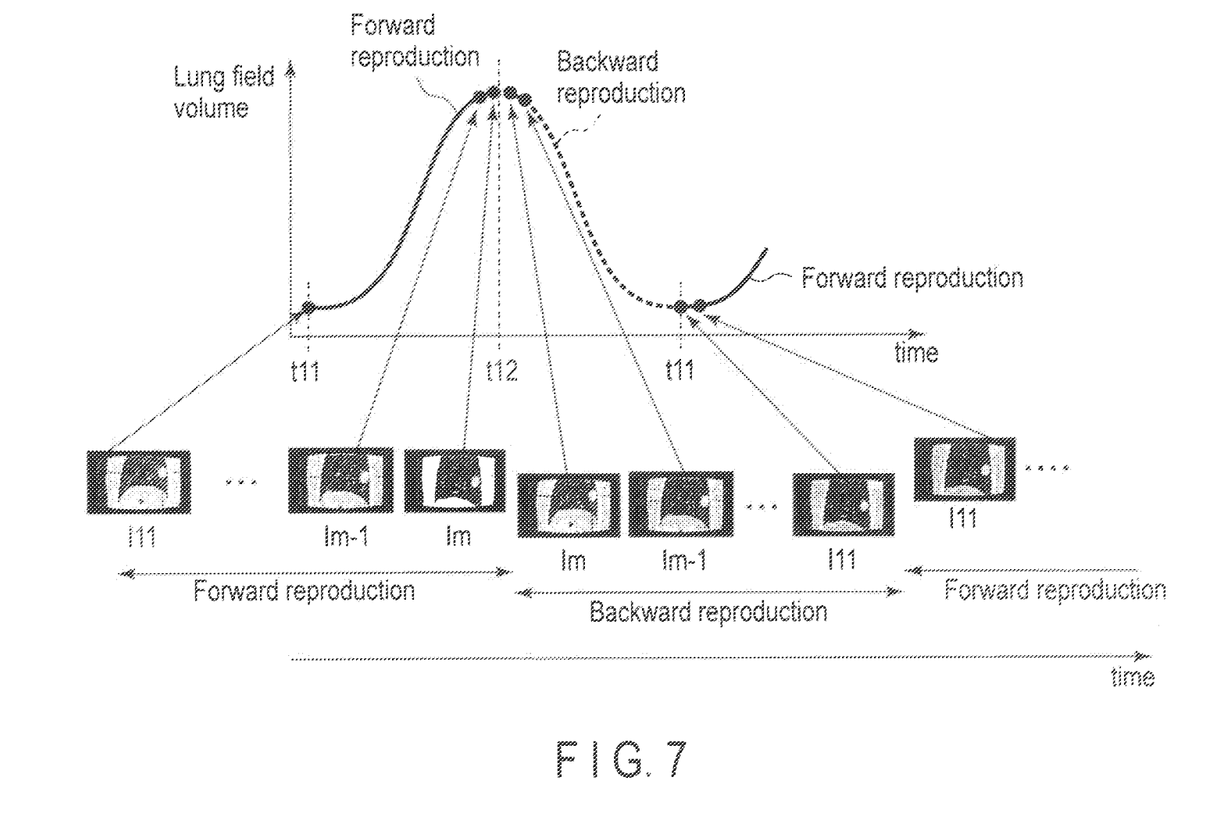
FIG. 7 is a graph for explaining respiratory gated alternate reproduction in FIG. 2.

As shown in FIGS. 6 and 7, in the respiratory gated alternate reproduction scheme, the apparatus repeats alternate reproduction of moving images in part of the entire period (t01 to t02) of a 4D dynamic scan, only within the half respiratory cycle (t11 to t12) in this case, which is specified by the maximum value/minimum value specifying unit 123. The apparatus alternately connects partial respiratory waveform curves, in the forward and backward directions, which correspond to the half respiratory cycle of the 4D dynamic scan stored in the respiratory waveform storage unit 121, and displays the resultant data on the screen of the display 117, together with a moving image.

More specifically, as shown in FIG. 2, the apparatus causes the reproduction controller 118 to read out respiratory waveform data from the respiratory waveform storage unit 121 (S04). The reproduction controller 118 searches for respiratory waveform data corresponding to the entire period (t01 to t02) of the 4D dynamic scan (S05). If there is respiratory waveform data corresponding to the entire period (t01 to t02) of the 4D dynamic scan, the apparatus displays the corresponding respiratory waveform curve on the display 117 (S06).

If there is no respiratory waveform data corresponding to the entire period (t01 to t02) of the 4D dynamic scan, the apparatus causes the image processing unit 115 to read out n volume data sets corresponding to the entire period (t01 to t02) of the 4D dynamic scan from the volume data storage unit 113. The image processing unit 115 extracts a lung field region from each of the n volume data sets by, for example, threshold processing for a CT value, and calculates the volume of the region as respiratory index data. The apparatus arranges a plurality of calculated lung field volumes (S09) in the forward direction following the same time course as that in the acquisition of image data, and performs interpolation as needed, thereby generating a volume curve as a respiratory waveform curve (S10). The apparatus displays the generated respiratory waveform curve on the display 117 (S06).

The maximum value/minimum value specifying unit 123 specifies the maximum and minimum values of the respiratory waveform curve (S07). For example, the time when the respiratory index exhibits the minimum value represents the expiratory bottom time, whereas the time when the respiratory index exhibits the maximum value represents the inspiratory peak time. The period between the expiratory bottom time and the inspiratory peak time represents almost half of a respiratory cycle. Note that it is possible to simply search for maximum and minimum values or calculate maximal and minimal values from differential values by waveform fitting.

The image processing unit 115 alternately connects a partial respiratory waveform in the forward direction which corresponds to an almost half respiratory cycle from the calculated minimum value to the calculated maximum value and a respiratory waveform in the backward direction which is obtained by inverting the partial respiratory waveform following the time course (S08).

As shown in FIG. 7, the apparatus reproduces medical images of frames I11 to Im included in a period (t11 to t12) corresponding to almost the half respiratory cycle as part of the entire period (t01 to t02) of a 4D dynamic scan, in accordance with the respective time codes, in real time in the forward direction following the same time course as that in the acquisition of image data (forward reproduction). The apparatus then reproduces the images in real time in the backward direction following the time course opposite to that in the acquisition of image data (backward reproduction), thus alternately repeating forward reproduction and backward reproduction in the above manner (S03). The apparatus displays the respiratory waveform curve generated in step S08 on the screen of the display 117, together with a moving image. For example, the respiratory waveform curve generated in the forward direction following the same time course as that in the acquisition of image data is displayed in solid line, whereas the respiratory waveform curve generated in the backward direction following the time course opposite to that in the acquisition of image data is displayed in dotted line.

The moving images alternately reproduced within this limited almost half respiratory cycle are approximate to those repeatedly reproduced in one respiratory cycle. In alternate reproduction within the limited almost half cycle, the final frame Im of the moving image is continuous with the final frame Im, and the first frame I11 is continuous with the first frame I11. Obviously, therefore, the tissue distribution undergoes no displacement on the screen. This maintains visual continuity of motion. When, for example, observing a moving image while paying attention to a tumor, the observer need not greatly move his/her line of sight.

Assume that when reproducing a moving image in one pseudo respiratory cycle in the respiratory gated alternate reproduction scheme, there is no volume data at an expected time. In this case, it is possible to obtain such data from an adjacent volume. This technique is effective for the reproduction of discrete data, unequally-spaced data, or the like. It is also possible to focus on an object designated by the user at the time of reproduction or automatically extracted based on tissue density differences and to display a slice which always displays the object.

Using the above means will eliminate stepped portions at the time of reproduction, thereby eliminating any feeling of strangeness. When observing a tumor or the like, the observer often sees the motion by using MPR images. In this case, the presence of stepped portions makes it difficult to comprehend the motion. However, reproduction by this technique can be expected to facilitate comprehension of the motion. In addition, there is no need to execute scanning throughout one respiratory cycle, and hence it is possible to reduce the radiation exposure.

Figure 8:
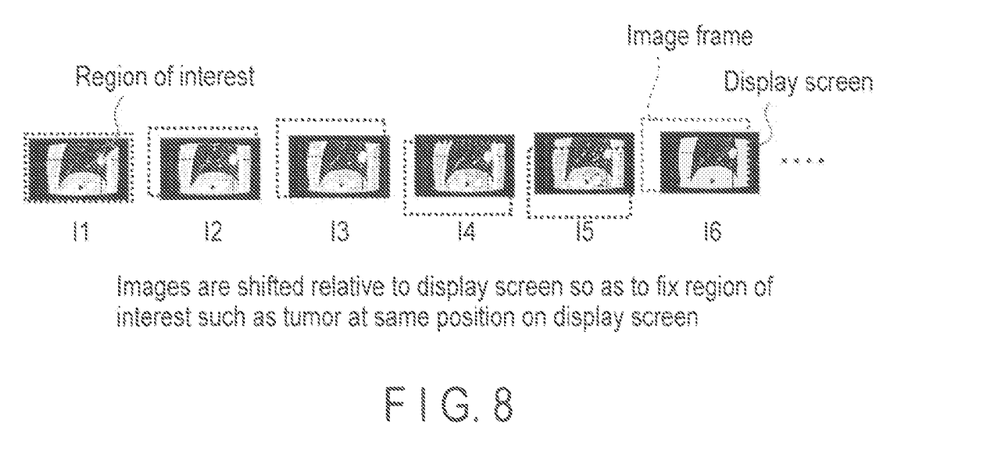
FIG. 8 is a view for explaining image frame shift processing for a display screen according to this embodiment.

FIG. 8 shows image frame shift processing for the display screen in this embodiment. Image frame shift processing is the processing of shifting the frame position of each medical image relative to the image display screen of the display 117 to fix a region of interest such as a tumor at a specific position within the image display screen. First of all, the image processing unit 115 extracts a region of interest such as a tumor from each of a series of medical images constituting a moving image to be displayed by threshold processing or the like, and calculates the position of the extracted region of interest, e.g., the barycentric position. The reproduction controller 118 performs coordinate conversion of each medical image to match the calculated position of the region of interest in each medical image with the specific position on the image display screen. The specific position on the image display screen is typically set to the position designated by the operator, the central position of the image display screen, or the position on the display screen at which, for example, the barycentric position of a region of interest in the first frame of a series of medical images constituting a moving image to be displayed. The reproduction controller 118 performs read control of the volume data storage unit 113 for the medical image data having undergone coordinate conversion. This will reproduce a moving image while a region of interest such as a tumor is fixed at a specific position in the image display screen of the display 117. When the image interpreter visually recognizes the tumor on the moving image, the load on the interpreter can be reduced in terms of the movement of the line of sight within the screen.

Figure 9:
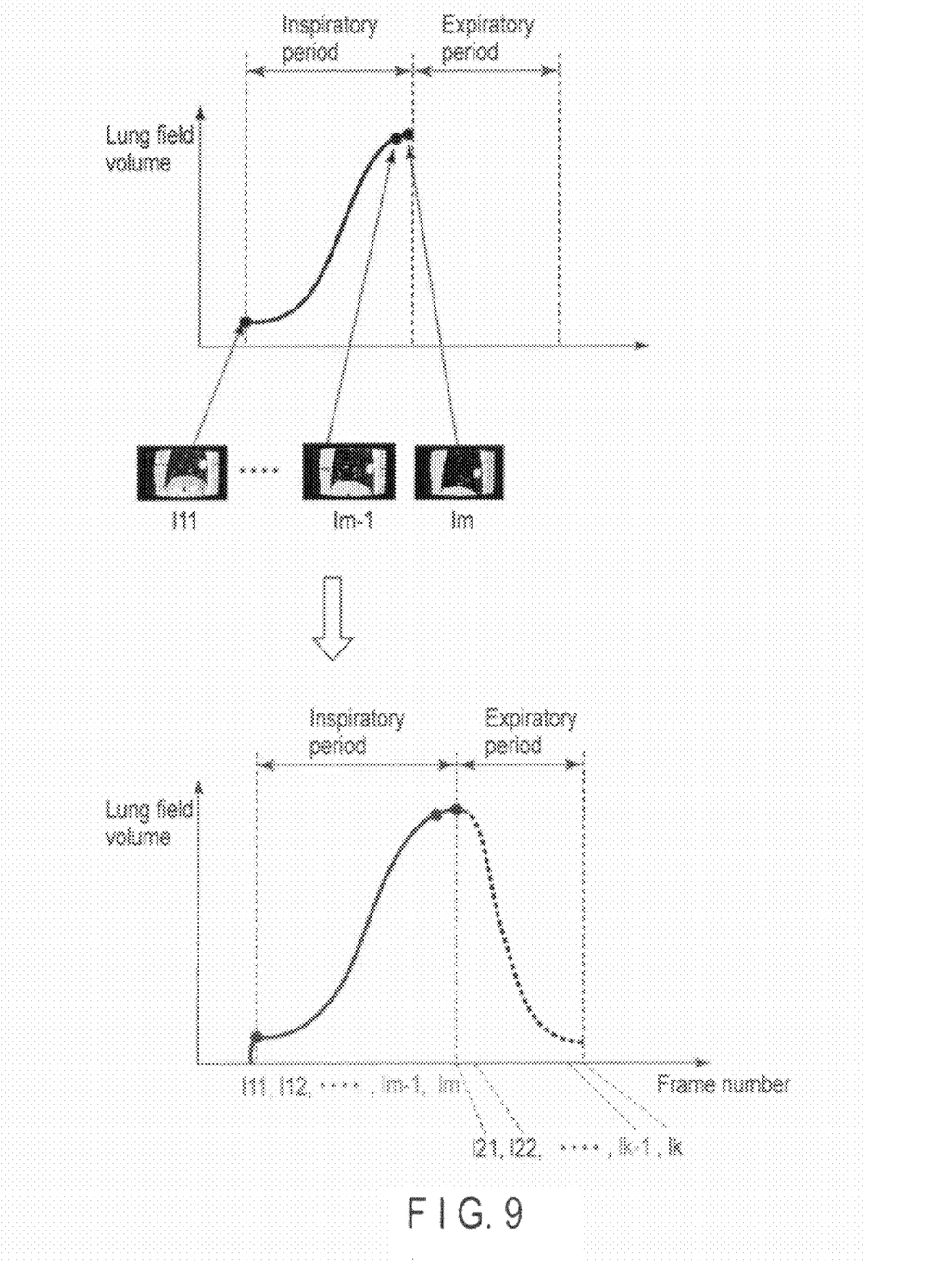
FIG. 9 is a view for explaining another reproduction technique according to this embodiment.

According to the above description, a series of images acquired in an inspiratory period are alternately reproduced in the forward and backward directions. In other words, a series of images corresponding to an expiratory period in which no images have been acquired are generated by rearranging the series of images actually acquired in the inspiratory period in the backward direction. As shown in FIG. 9, it is possible to generate a series of images 121, 122, ..., Ik corresponding to an expiratory period by inverse arrangement, interpolation, or thinning processing for a series of images I11, I12, ..., Im acquired in an inspiratory period. Typically, an image in an expiratory period is generated by weighted addition processing with weights corresponding to time intervals for two or three or more frames on the two sides of the image. The interpolation processing technique to be used is not limited to this, and an arbitrary technique can be used. It is also possible to generate a series of images corresponding to an expiratory period by partly thinning a series of images actually acquired in an inspiratory period at predetermined intervals. The apparatus then alternately displays the series of actually acquired images corresponding to an inspiratory period and the series of generated images corresponding to an expiratory period.

In addition, a series of images corresponding to an inspiratory period which have not been actually acquired are not always generated from a series of actually acquired images corresponding to an inspiratory period. For example, a series of standard model images corresponding to an inspiratory period are prepared in advance. A series of model images most approximate to an object are then selected in accordance with the average cardiac rate, age, sex, physique, lung volume and vital capacity etc of the object. The apparatus then alternately displays the series of actually acquired images corresponding to an inspiratory period and the selected series of model images corresponding to an expiratory period.

According to the above description, although a series of images are actually acquired in a partial period of a respiratory cycle, e.g., an inspiratory period, no images are acquired in an expiratory period. It is however possible to acquire a series of images at irregular intervals throughout at least one cycle of respiratory motion and generate a series of medical images arranged at predetermined intervals from the series of actually acquired images by interpolation processing.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image display apparatus comprising:
    an image storage unit configured to store data of a series of medical images constituting a moving image associated with an object; and
    a reproduction control unit configured to perform read control of the image storage unit to alternately and repeatedly reproduce and display a part of the medical images corresponding to a partial period in one cycle associated with cyclic motion of the object in a forward direction and a backward direction.

2. The apparatus of claim 1, wherein the cyclic motion is respiratory motion of the object, and the partial period is one of an inspiratory period and an expiratory period of the respiratory motion.

3. The apparatus of claim 2, further comprising a period specifying unit configured to specify one of the inspiratory period and the expiratory period in accordance with a minimal value and maximal value of a respiratory waveform representing the respiratory motion.

4. The apparatus of claim 2, further comprising:
a respiratory waveform generation unit configured to extract a lung field region of the object from each of the medical images by image processing and generate temporal changes in one of an area and a volume of the lung field region as a respiratory waveform representing the respiratory motion; and
a period specifying unit configured to specify one of the inspiratory period and the expiratory period in accordance with a minimal value and maximal value of a respiratory waveform representing the respiratory motion.

5. The apparatus of claim 2, further comprising an image display unit which alternately displays a respiratory waveform representing the respiratory motion corresponding to one of the inspiratory period and the expiratory period and an inverted respiratory waveform, together with the medical images.

6. A medical image display apparatus comprising:
an image storage unit configured to store data of a series of medical images constituting a moving image corresponding to a partial period in one cycle associated with cyclic motion associated with an object; and
a reproduction control unit configured to perform read control of the image storage unit to alternately and repeatedly reproduce and display the series of medical images in a forward direction and a backward direction.

7. The apparatus of claim 6, wherein the cyclic motion is respiratory motion of the object, and the partial period is one of an inspiratory period and an expiratory period of the respiratory motion.

8. An X-ray computed tomography apparatus comprising:
an X-ray tube;
an X-ray detector;
a data acquisition unit configured to acquire projection data associated with an object via the X-ray detector;
a reconstruction unit configured to reconstruct data of a series of medical images constituting a moving image associated with the object based on the acquired projection data;
an image storage unit configured to store the data of the series of medical images; and
a reproduction control unit configured to perform read control of the image storage unit to alternately and repeatedly reproduce and display a part of the medical images corresponding to a partial period in one cycle associated with cyclic motion of the object in a forward direction and a backward direction.

9. The apparatus of claim 8, wherein the cyclic motion is respiratory motion of the object, and the partial period is one of an inspiratory period and an expiratory period of the respiratory motion, and the apparatus further comprises a control unit configured to control the data acquisition unit in synchronism with the respiratory motion to cause the data acquisition unit to acquire the projection data within one of the limited inspiratory period and the limited expiratory period.

10. The apparatus of claim 9, further comprising an image display unit which alternately displays a respiratory waveform representing the respiratory motion corresponding to one of the inspiratory period and the expiratory period and an inverted respiratory waveform, together with the medical images.

11. An X-ray computed tomography apparatus comprising:
a data acquisition unit configured to acquire projection data associated with an object;
a reconstruction unit configured to reconstruct data of a series of medical images constituting a moving image corresponding to a partial period in one cycle associated with respiratory motion associated with the object based on the acquired projection data;
an image storage unit configured to store the data of the series of medical images; and
a reproduction control unit configured to perform read control of the image storage unit to alternately and repeatedly reproduce and display the series of medical images in a forward direction and a backward direction.

12. A medical image display apparatus comprising:
an image storage unit configured to store data of a first series of medical images constituting a moving image corresponding to a partial period in one cycle associated with cyclic motion of an object;
an image generation unit configured to generate a second series of medical images by performing inverse arrangement processing and one of interpolating processing and thinning processing for the first series of medical images, the second series of medical images being stored at the image storage unit; and
a reproduction control unit configured to perform read control of the image storage unit to alternately display the first series of medical images and the second series of medical images.

13. The apparatus of claim 12, wherein the cyclic motion is respiratory motion of the object, and the partial period is one of an inspiratory period and an expiratory period of the respiratory motion.

14. A medical image display apparatus comprising:
an image storage unit configured to store data of a first series of medical images arranged at irregular time intervals throughout at least one cycle associated with cyclic motion of an object;
an image generation unit configured to generate a second series of medical images arranged at predetermined time intervals by performing interpolation processing for the first series of medical images, the second series of medical images being stored at the image storage unit; and
a reproduction control unit configured to perform read control of the image storage unit to repeatedly display the second series of medical images.

* * * * *